(12) United States Patent
Torai et al.

(10) Patent No.: US 11,459,534 B2
(45) Date of Patent: Oct. 4, 2022

(54) ORGAN CONTAINER

(71) Applicant: SCREEN HOLDINGS CO., LTD., Kyoto (JP)

(72) Inventors: Shinji Torai, Kyoto (JP); Syuhei Yoshimoto, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 345 days.

(21) Appl. No.: 16/765,283

(22) PCT Filed: Oct. 1, 2018

(86) PCT No.: PCT/JP2018/036652
§ 371 (c)(1),
(2) Date: May 19, 2020

(87) PCT Pub. No.: WO2019/106936
PCT Pub. Date: Jun. 6, 2019

(65) Prior Publication Data
US 2020/0308520 A1    Oct. 1, 2020

(30) Foreign Application Priority Data

Nov. 28, 2017  (JP) .............................. JP2017-227718

(51) Int. Cl.
*A01N 1/02* (2006.01)
*C12M 3/00* (2006.01)
(Continued)

(52) U.S. Cl.
CPC ........... *C12M 21/08* (2013.01); *A01N 1/0247* (2013.01); *C12M 23/06* (2013.01); *C12M 23/14* (2013.01); *C12M 23/26* (2013.01); *C12M 23/38* (2013.01)

(58) Field of Classification Search
CPC .............................. C12M 21/08; A01N 1/0247
See application file for complete search history.

(56) References Cited

U.S. PATENT DOCUMENTS 6,100,082 A * 8/2000 Hassanein ................ A01N 1/02
435/284.1
10,034,738 B2 * 7/2018 Thavandiran .......... C12M 35/04
(Continued)

FOREIGN PATENT DOCUMENTS

CN          86203016 U       12/1986
CN          2896900 Y         5/2007
(Continued)

OTHER PUBLICATIONS

International Search Report issued in corresponding International Patent Application No. PCT/JP2018/036652, dated Nov. 27, 2018, with English translation.

(Continued)

*Primary Examiner* — Jonathan M Hurst
(74) *Attorney, Agent, or Firm* — McDermott Will & Emery LLP

(57) ABSTRACT

An organ container includes flexible films and a tube holder. The films hold an organ in contact with the surface of the organ. The tube holder holds tubes that extend between the organ in the films and an outside of the films. This makes it possible to hold and preserve the organ while allowing a liquid to be perfused through the organ via the tubes. It is also possible to reduce movements of the organ relative to the organ container and to reduce damage to the organ.

5 Claims, 6 Drawing Sheets

(51) Int. Cl.
  *C12M 1/12* (2006.01)
  *C12M 1/00* (2006.01)

(56) References Cited

U.S. PATENT DOCUMENTS

| | | | |
|---|---|---|---|
| 2005/0147958 A1* | 7/2005 | Hassanein | A01N 1/0247 435/284.1 |
| 2006/0121439 A1* | 6/2006 | Baker | A01N 1/0247 435/284.1 |
| 2007/0184545 A1* | 8/2007 | Plaats | A01N 1/0273 435/284.1 |
| 2011/0065169 A1* | 3/2011 | Steen | A01N 1/02 435/284.1 |
| 2015/0289940 A1 | 10/2015 | Campsen et al. | |
| 2016/0113269 A1* | 4/2016 | Woodard | A01N 1/0273 435/284.1 |
| 2021/0235691 A1* | 8/2021 | Collette | A01N 1/0273 |
| 2022/0022448 A1* | 1/2022 | Kasamatsu | A01N 1/0247 |

FOREIGN PATENT DOCUMENTS

| | | |
|---|---|---|
| CN | 201345874 Y | 11/2009 |
| CN | 202232704 U | 5/2012 |
| CN | 103688924 B | 7/2015 |
| CN | 205962505 U | 2/2017 |
| JP | 47-040995 Y1 | 12/1972 |
| JP | 02-111701 A | 4/1990 |
| JP | 03-151303 A | 6/1991 |
| JP | 06-016501 A | 1/1994 |
| JP | 07-101801 A | 4/1995 |
| JP | 07-101802 A | 4/1995 |
| JP | 2000-309377 A | 11/2000 |
| JP | 2001-039473 A | 2/2001 |
| JP | 2003-267471 A | 9/2003 |
| JP | 2017-039497 A | 2/2017 |
| WO | 2014/194349 A1 | 12/2014 |

OTHER PUBLICATIONS

Extended European Search Report issued in corresponding European Patent Application No. 18884777.6-1126, dated Feb. 17, 2021.
Chinese Office Action issued in corresponding Chinese Patent Application No. 201880072728.1, dated Apr. 29, 2021.

* cited by examiner

ORGAN CONTAINER

CROSS REFERENCE TO RELATED APPLICATIONS

This application is the U.S. National Phase under 35 U.S.C. § 371 of International Patent Application No. PCT/JP2018/036652, filed on Oct. 1, 2018, which claims the benefits of Japanese Patent Application No. 2017-227718, filed on Nov. 28, 2017 the entire contents of which are hereby incorporated by reference.

TECHNICAL FIELD

The present invention relates to an organ container that accommodates an organ.

BACKGROUND ART

In organ transplant operations such as liver transplantation, an organ is temporarily preserved outside the body during the period from when the organ is removed from the donor to when the organ is transplanted into the recipient. At this time, the organ is connected to tubes so that a preservation solution is perfused through the organ in order to prevent the organ from becoming ischemic. In the case where the removal of the organ from the donor and the transplantation of the organ into the recipient are conducted at different places, the organ also needs to be transported while being preserved.

For example, Patent Document 1 describes a conventional device for preserving an organ outside the body.

PRIOR ART DOCUMENT

Patent Document

Patent Document 1: Japanese Patent Application Laid-Open No. H3-151303

SUMMARY OF INVENTION

Problems to be Solved by Invention

The device described in Patent Document 1 uses a hammock made of hydrophobic cloth to hold an organ. However, merely placing the organ on the hammock as in Patent Document 1 increases the likelihood of the position of the organ being shifted relative to the hammock. It is thus difficult to transport the organ from the donor to the recipient without damage.

The present invention has been made in view of such circumstances, and it is an object of the present invention to provide an organ container that is capable of preserving an organ while allowing a liquid to be perfused through the organ and that is also capable of reducing the occurrence of a shift in the position of the organ and damage to the organ.

Means for Solving Problems

In order to solve the above-described problem, a first aspect of the present invention is an organ container for containing an organ, and includes a flexible film that holds the organ, an opening and closing part that opens and closes an edge of the film, and a tube holder that holds a tube extending between the organ in the film and an outside of the film.

A second aspect of the present invention is the organ container according to the first aspect, wherein the film includes a sheet-like first film that covers a lower part of the organ, and a sheet-like second film that covers an upper part of the organ, and the organ is sandwiched and held between the first film and the second film.

A third aspect of the present invention is the organ container according to the second aspect, wherein the opening and closing part includes a ring-shaped lower frame that supports peripheral portions of the first film and the second film from an underside, the peripheral portions overlapping each other, and a ring-shaped upper frame that sandwiches the peripheral portions of the first film and the second film with the lower frame.

A fourth aspect of the present invention is the organ container according to the third aspect. This organ container further includes a locking part that locks and fixes the lower frame and the upper frame to each other by bringing the lower frame and the upper frame close to each other.

A fifth aspect of the present invention is the organ container according to the third or fourth aspect, wherein the tube holder has a groove provided in at least one of an upper face of the lower frame and a lower face of the upper frame, and the tube is fitted in the groove.

A sixth aspect of the present invention is the organ container according to the fifth aspect, wherein the tube holder has a plurality of grooves, each of which is the groove, and the plurality of grooves are provided at intervals in a circumferential direction.

A seventh aspect of the present invention is the organ container according to the first aspect. This organ container includes a pouch-like film bag formed of the film. The organ is accommodated in the film bag.

An eighth aspect of the present invention is the organ container according to the seventh aspect, wherein the opening and closing part is an openable and closable chuck provided at an opening of the film bag.

A ninth aspect of the present invention is the organ container according to the eighth aspect, wherein the chuck includes a pair of chuck members capable of becoming in intimate contact with and separated from each other, the tube holder has a groove provided in at least one of the pair of chuck members, and the tube is fitted in the groove.

A tenth aspect of the present invention is the organ container according to the seventh aspect, wherein the opening and closing part includes a drawstring capable of tightening and loosening the opening of the film bag.

An eleventh aspect of the present invention is the organ container according to any one of the first to tenth aspects, wherein the film is made of a resin.

Effects of Invention

According to the first to eleventh aspects of the present invention, it is possible to hold the organ while allowing a liquid to be perfused through the organ via the tube. It is also possible to reduce the movement of the organ relative to the organ container and to reduce damage to the organ.

In particular, according to the second aspect, using the separate first and second films allows these films to become wide open vertically. This facilitates putting the organ into and out of the organ container.

In particular, according to the fourth aspect, the lower frame and the upper frame can be fixed to each other by one touch without use of a fastening device such as a screw.

In particular, according to the fifth aspect, it is possible to hold the tube while reducing a shift in the position of the tube.

In particular, according to the sixth aspect, the tube can be fixed in any of the grooves prepared in advance.

In particular, according to the seventh aspect, the number of components of the organ container can be reduced.

In particular, according to the ninth aspect, it is possible to hold the tube while reducing a shift in the position of the tube.

DESCRIPTION OF EMBODIMENTS

Hereinafter, embodiments of the present invention will be described with reference to the drawings.

In the present application, donors and recipients may be humans, or may be non-human animals. That is, in the present application, organs including livers may be human organs, or may be organs of non-human animals. The non-human animals may be rodents such as mice and rats; ungulates such as pigs, goats, and sheep; non-human primates such as chimpanzees; or other non-human mammals, or may be nonmammalian animals.

1. First Embodiment

Figure 1:
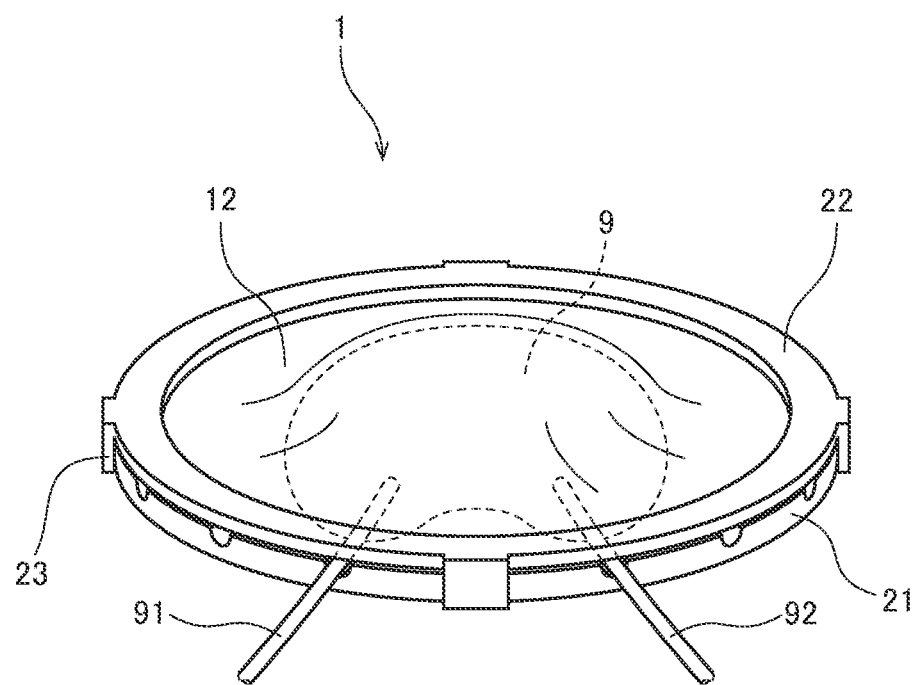
FIG. 1 is a perspective view of an organ container according to a first embodiment.
Figure 2:
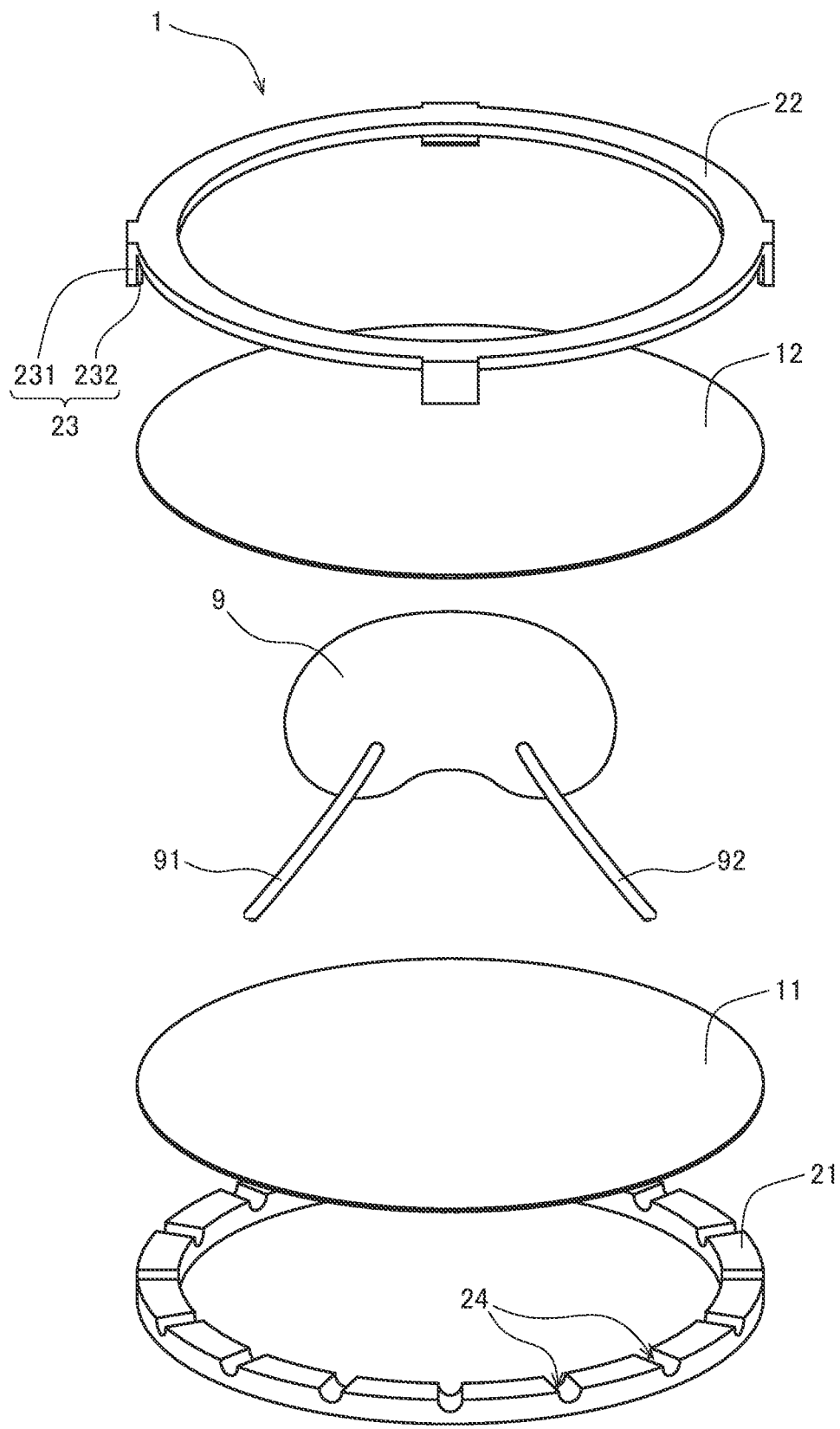
FIG. 2 is an exploded perspective view of the organ container according to the first embodiment.

FIG. 1 is a perspective view of an organ container 1 according to a first embodiment. FIG. 2 is an exploded perspective view of the organ container 1.

This organ container 1 is a container that temporarily accommodates a liver 9 removed from the donor in a liver transplantation operation. The liver 9 after being removed from the donor needs to be preserved while a preservation solution is being perfused therethrough, during the period until when the liver is transplanted into the recipient. For this reason, the liver 9 is connected to a supplying tube 91 for supplying the preservation solution and a drain tube 92 for draining the preservation solution. The supplying tube 91 is connected to, for example, the portal vein or hepatic artery of the liver 9 through a catheter. The drain tube 92 is connected to, for example, the suprahepatic inferior vena cava or infrahepatic inferior vena cava of the liver 9 through a catheter.

As illustrated in FIGS. 1 and 2, the organ container 1 according to the present embodiment includes a first film 11, a second film 12, a lower frame 21, and an upper frame 22.

The first film 11 is a sheet film that covers the lower part of the liver 9. The second film 12 is a sheet film that covers the upper part of the liver 9. The first film 11 and the second film 12 are both made of a flexibly deformable material. The first film 11 and the second film 12 according to the present embodiment have a circular shape when viewed from above. Alternatively, the first film 11 and the second film 12 may have other shapes such as an oval shape. The first film 11 and the second film 12 have approximately the same size and are larger than the liver 9 when viewed from above. The upper face of the first film 11 comes in contact with the lower part of the liver 9. The lower face of the second film 12 comes in contact with the upper part of the liver 9.

That is, the liver 9 is sandwiched and held between the first film 11 and the second film 12. The first film 11 and the second film 12 have flexibility, and therefore each become deformed depending on the surface shape of the liver 9.

The material for the first film 11 and the second film 12 is a resin having bioadaptability and sterilization retention properties and also having flexibility. For example, polypropylene, polyethylene, polyurethane, polyvinylidene chloride, polystyrene, an elastomeric resin, silicon, rubber, a gel material, or polyamide may be used as the material for the first film 11 and the second film 12. The first film 11 and the second film 12 may be permeable to the preservation solution, or may be impermeable to the preservation solution. Whether the first film 11 and the second film 12 have fluid permeability may be appropriately selected according to the circumstances where these films are used. The first film 11 and the second film 12 may also have the property of being permeable to gases such as oxygen.

The lower frame 21 is a ring-shaped member arranged below the first film 11. The upper face of the lower frame 21 comes in contact with the lower face of a peripheral portion of the first film 11 and supports the peripheral portion of the first film 11 from the underside. The upper frame 22 is a ring-shaped member arranged above the second film 12. The lower face of the upper frame 22 comes in contact with the upper face of a peripheral portion of the second film 12. The lower frame 21 and the upper frame 22 are rigid bodies that do not easily become deformed. That is, the lower frame 21 and the upper frame 22 are made of a material having less flexibility than the first film 11 and the second film 12. The material for the lower frame 21 and the upper frame 22 is for example, a resin or a metal.

In the present embodiment, the lower frame 21 and the upper frame 22 serve as an opening and closing part that opens and closes the edges of the first film 11 and the second film 12. In the example illustrated in FIGS. 1 and 2, the lower frame 21 and the upper frame 22 have a circular shape when viewed from above. Alternatively, the lower frame 21 and the upper frame 22 may have other shapes such as a rectangular shape.

In use of the organ container 1, the first film 11 is first arranged on the upper side of the lower frame 21. Then, the liver 9 removed from the donor is placed on the center of the upper face of the first film 11. Next, the upper part of the liver 9 is covered with the second film 12. At this time, the peripheral portion of the first film 11 and the peripheral portion of the second film 12 are brought to overlap one on the other. That is, the upper face of the peripheral portion of the first film 11 and the lower face of the peripheral portion of the second film 12 are brought into contact with each other. Alternatively, the lower frame 21 and the first film 11 may be fixed beforehand to each other with a fastening device such as a clip.

The upper frame 22 includes a plurality of locking parts 23. Each locking part 23 has, for example, an arm 231 that extends downward from the edge of the upper frame 22, and a claw 232 provided at the tip of the arm 231. When the upper frame 22 is brought closer to the lower frame 21 from above, the locking parts 23 are locked to the lower frame 21.

Accordingly, the lower frame 21 and the upper frame 22 are fixed to each other as illustrated in FIG. 1.

The aforementioned peripheral portions of the first film 11 and the second film 12 are sandwiched between the upper face of the lower frame 21 and the lower face of the upper frame 22. Accordingly, the peripheral portions of the first film 11 and the second film 12 are closed. As a result, the liver 9 is held between the first film 11 and the second film 12.

The lower frame 21 has a plurality of grooves 24. The grooves 24 are provided at intervals (e.g., equal intervals) in the circumferential direction in the upper face of the lower frame 21. Each groove 24 extends radially from the inner peripheral edge of the upper face of the lower frame 21 to the outer peripheral edge thereof. Each of the supplying tube 91 and the drain tube 92 connected to the liver 9 is fitted in one of the grooves 24 via the first film 11. The supplying tube 91 and the drain tube 92 extend from the liver 9 held inside the first film 11 and the second film 12 to the outside of the first film 11 and the second film 12 through the grooves 24. This structure reduces shifts in the positions of the supplying tube 91 and the drain tube 92.

In the present embodiment, these grooves 24 serve as a tube holder that holds the supplying tube 91 and the drain tube 92. Alternatively, the grooves 24 may be provided in the lower face of the upper frame 22. As another alternative, the grooves 24 may be provided in both the upper face of the lower frame 21 and the lower face of the upper frame 22.

In the case of transplanting the liver 9 held by the organ container 1 into the recipient, the locking parts 23 are first detached from the lower frame 21. Then, the lower frame 21 and the upper frame 22 are vertically separated from each other. Next, the peripheral portions of the first film 11 and the second film 12 are opened, and the second film 12 is stripped off. Thereafter, the liver 9 is taken out of the upper face of the first film 11 and transplanted into the recipient.

As described above, this organ container 1 is capable of holding not only the liver 9 but also the supplying tube 91 and the drain tube 92. Thus, the organ container 1 can preserve the liver 9 while allowing the preservation solution to be perfused through the liver 9 via the supplying tube 91 and the drain tube 92. Moreover, this organ container 1 accommodates the liver 9 between the first film 11 and the second film 12, both having flexibility. The organ container 1 holds the liver 9 by bringing the first film 11 and the second film 12 into contact with the surface of the liver 9. Accordingly, the organ container 1 can preserve the liver 9 while reducing the movement of the liver 9 relative to the first film 11 and the second film 12. The organ container 1 can also reduce damage to the surface of the liver 9 more than in the case where the liver 9 is held by a rigid body.

In particular, the present embodiment uses the two separate films 11 and 12 to hold the liver 9. This allows the first film 11 and the second film 12 to become wide open vertically as illustrated in FIG. 2. Thus, the liver 9 can be put in and out of the organ container 1 with ease.

The lower frame 21 and the upper frame 22 according to the present embodiment can be fixed to each other by one touch with the locking parts 23 by simply bringing them close to each other. This eliminates the need to use a fastening device such as a screw to fix the lower frame 21 and the upper frame 22. Accordingly, the liver 9 removed from the donor can be speedily accommodated in the organ container 1. Alternatively, the locking parts 23 may be provided in the lower frame 21. As another alternative, the locking parts 23 may be omitted, and the lower frame 21 and the upper frame 22 may be fixed to each other with a fastening device such as a screw or a clip.

2. Second Embodiment

Figure 3:
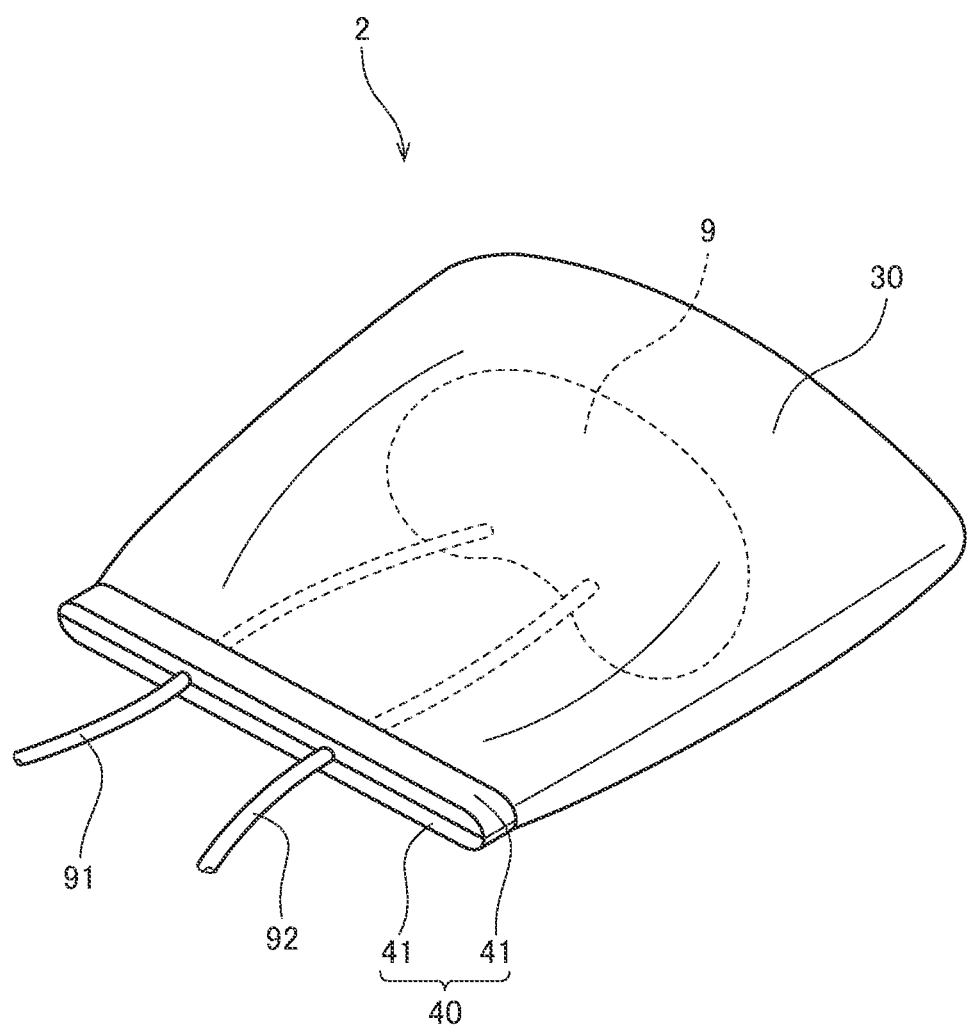
FIG. 3 is a perspective view of an organ container according to a second embodiment.
Figure 4:
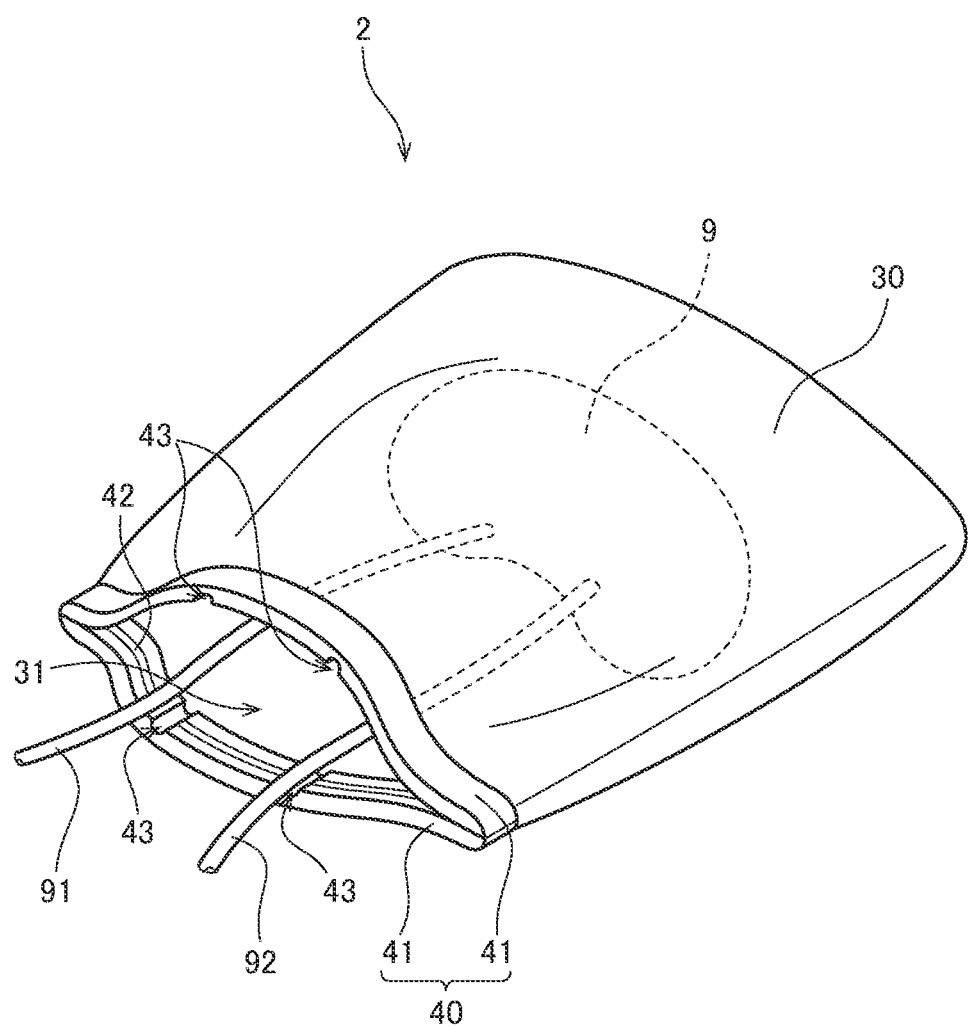
FIG. 4 is a perspective view of the organ container according to the second embodiment.

FIGS. 3 and 4 are perspective views of an organ container 2 according to a second embodiment. Like the organ container 1 of the first embodiment, this organ container 2 is also used to temporarily accommodate a liver 9 removed from a donor in a liver transplantation operation. FIG. 3 illustrates that an opening 31, through which the liver 9 is put in and out, is closed. FIG. 4 illustrates the opening 31 being open.

As illustrated in FIGS. 3 and 4, the organ container 2 includes a film bag 30, and a chuck 40 provided at the opening 31 of the film bag 30.

The film bag 30 is a pouch-like container formed of a film. The film forming the film bag 30 is made of a flexibly deformable material. The film bag 30 has, for example, a rectangular shape. The film bag 30 is slightly larger than the liver 9. The film bag 30 may have a bottom or side gusset. The liver 9 is accommodated inside the film bag 30. The film forming the film bag 30 comes in contact with the surface of the liver 9 and becomes deformed along the surface shape of the liver 9.

The material for the film forming the film bag 30 is a resin having bioadaptability and sterilization retention properties and also having flexibility. For example, polypropylene, polyethylene, polyurethane, polyvinylidene chloride, polystyrene, an elastomeric resin, silicon, rubber, a gel material, or polyamide may be used as the material for the film bag 30. The film bag 30 may be permeable to a preservation solution, or may be impermeable to the preservation solution. Whether the film bag 30 has fluid permeability may be appropriately selected according to the circumstances where the film bag 30 is used. The film bag 30 may also have the property of being permeable to gases such as oxygen.

The chuck 40 serves as an opening and closing part provided at the end of the film bag 30. The chuck 40 includes a pair of chuck members 41. The pair of chuck members 41 has minute projections and depressions 42 to be fitted in one another. When the pair of chuck members 41 is brought into contact with each other to apply pressure, the projections and depressions 42 of one of the chuck members 41 are fitted in the projections and depressions 42 of the other chuck member 41 so that the chuck members 41 come in intimate contact with each other. Accordingly, the film bag 30 is sealed. When the pair of chuck members 41 is separated from each other, the fitting of the projections and depressions 42 is released and the opening 31 of the film bag 30 becomes opened. The material for the chuck members 41 is, for example, a resin that is the same as the material for the film bag 30.

As illustrated in FIG. 4, each of the pair of chuck members 41 has two grooves 43. The two grooves 43 of one chuck member 41 are provided at positions opposite to the two grooves of the other chuck member 41. The supplying tube 91 and the drain tube 92 connected to the liver 9 are respectively fitted in the two grooves 43 of each chuck member 41. That is, the supplying tube 91 and the drain tube 92 extend from the liver 9 held inside the film bag 30 to the outside of the film bag 30 through the grooves 43. This structure reduces shifts in the positions of the supplying tube 91 and the drain tube 92.

In the present embodiment, these two grooves 43 serve as a tube holder that holds the supplying tube 91 and the drain tube 92. Alternatively, the two grooves 43 may be provided in only one of the pair of chuck members 41.

In use of the organ container 2, the pair of chuck members 41 is first separated from each other to open the end of the film bag 30. Then, the liver 9 removed from the donor is inserted into the film bag 30 through the space between the pair of chuck members 41. At this time, the liver 9 is connected to the supplying tube 91 and the drain tube 92. When the liver 9 is accommodated in the film bag 30, the supplying tube 91 and the drain tube 92 are fitted in the grooves 43 of the chuck members 41. Then, the pair of chuck members 41 is brought into intimate contact with each other. In this way, the film bag 30 is closed.

In the case of transplanting the liver 9 held in the film bag 30 into the recipient, the pair of chuck members 41 is first separated from each other to open the end of the film bag 30. Then, the supplying tube 91 and the drain tube 92 are removed from the grooves 43 of the chuck members 41. Thereafter, the liver 9 is taken out of the film bag 30 and transplanted into the recipient.

As described above, this organ container 2 is capable of holding not only the liver 9 but also the supplying tube 91 and the drain tube 92. Thus, the organ container 2 can preserve the liver 9 while allowing the preservation solution to be perfused through the liver 9 via the supplying tube 91 and the drain tube 92. Moreover, this organ container 1 accommodates the liver 9 inside the film bag 30 having flexibility. Then, the organ container 2 brings the inner face of the film bag 30 into contact with the surface of the liver 9 to hold the liver 9. Accordingly, the organ container 2 can preserve the liver 9 while reducing the movement of the liver 9 relative to the film bag 30. The organ container 2 can also reduce damage to the surface of the liver 9 more than in the case where the liver 9 is held by a rigid body.

In particular, the present embodiment uses the integrated film bag 30, instead of a plurality of films, to accommodate the liver 9. This reduces the number of components of the organ container 2. Besides, in the present embodiment, the film bag 30 and the chuck 40 are integrated with each other. This further reduces the number of components of the organ container 2. As a result, the organ container 2 can be handled with more ease.

Alternatively, the chuck 40 may be omitted, and the opening 31 of the film bag 30 may be sealed with a clip serving as an opening and closing part. In this case, the clip may be provided with grooves serving as a tube holder.

Figure 5:
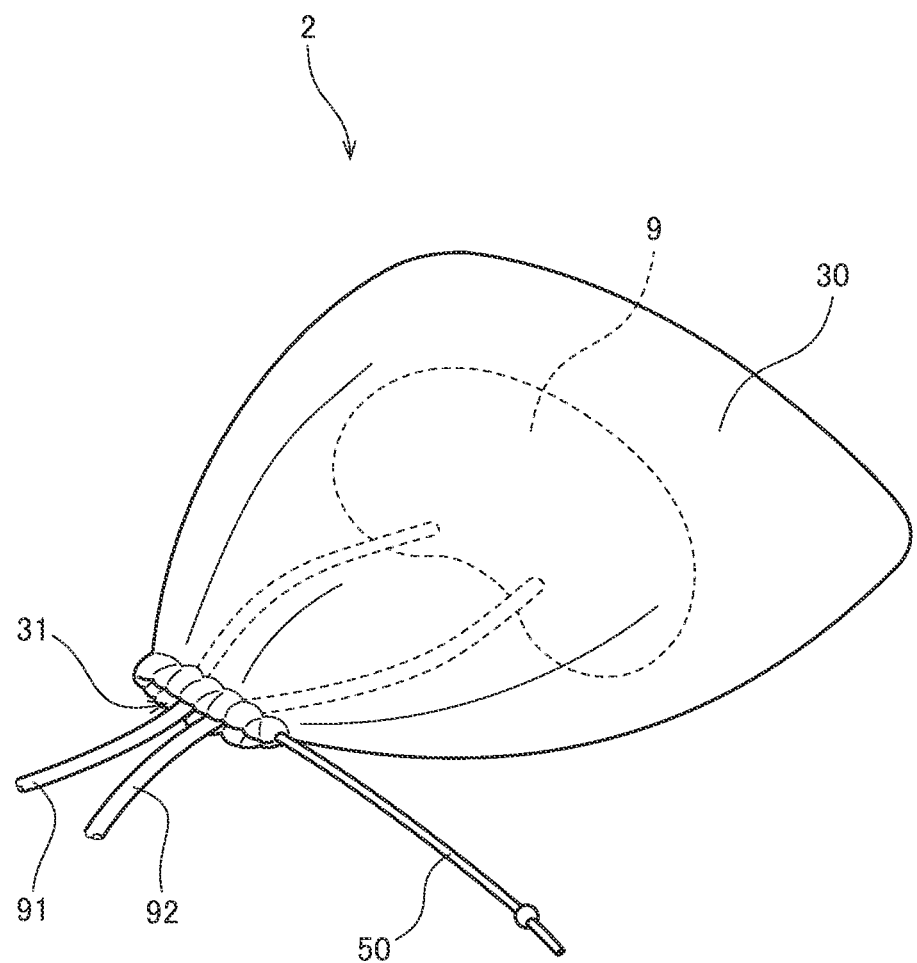
FIG. 5 is a perspective view of an organ container according to a variation.

As another alternative, the chuck 40 may be omitted, and a drawstring 50 serving as an opening and closing part may be provided in the opening of the film bag 30 as illustrated in FIG. 5. In the example in FIG. 5, the opening 31 of the film bag 30 can be tightened or loosened by pulling a drawstring 50, as in the case of a drawstring bag. In this case, the tightened opening 31 serves as a tube holder that holds the supplying tube 91 and the drain tube 92.

3. Variations

While the first and second embodiments of the present invention have been described thus far, the present invention is not limited to the embodiments described above.

Figure 6:
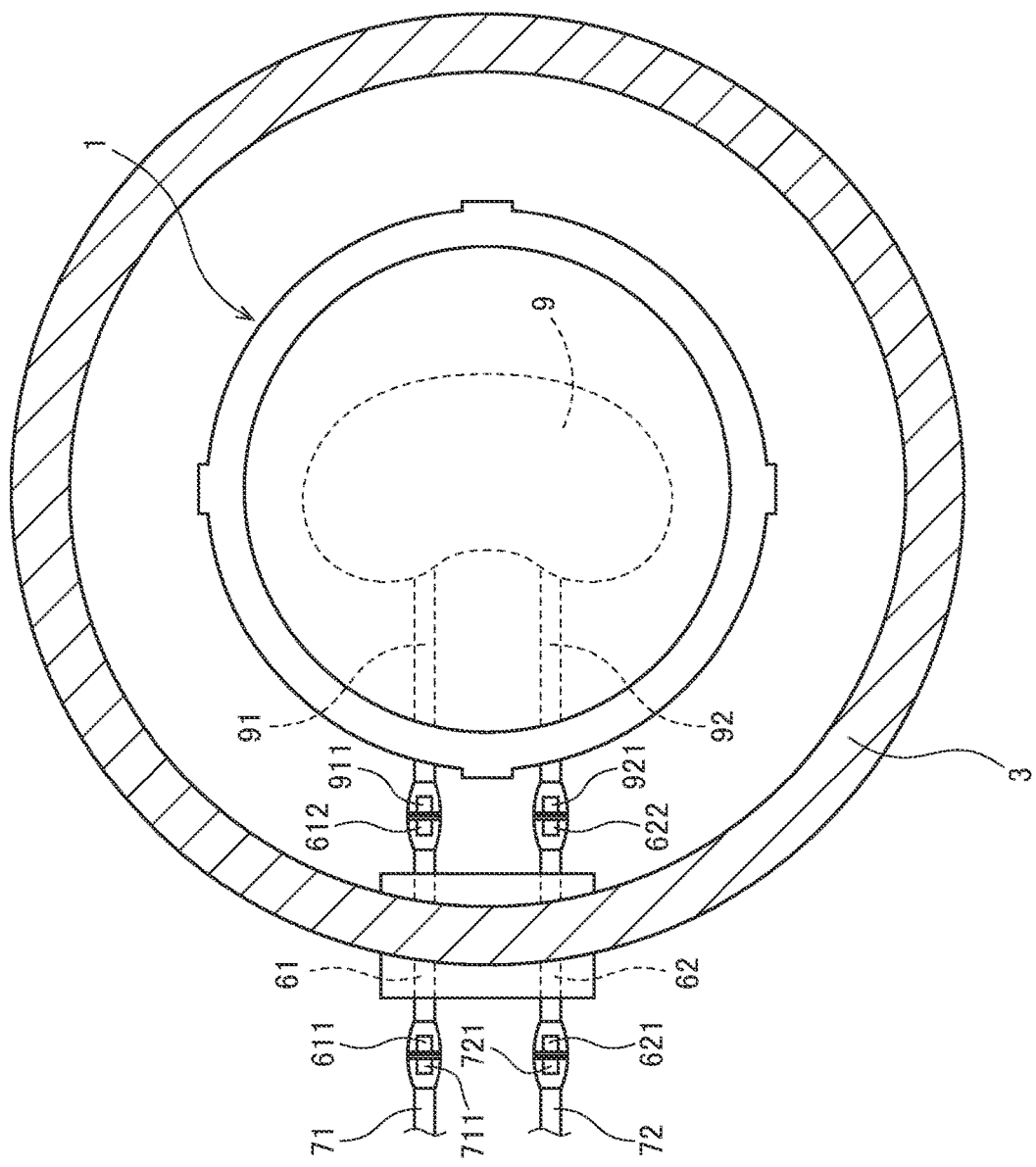
FIG. 6 is a perspective view of an organ container according to another variation.

As illustrated in FIG. 6, the organ container 1 according to the first embodiment may be accommodated inside an outer casing 3 having air-tightness or liquid-tightness. The outer casing 3 is preferably a rigid body that does not become easily deformed. With this structure, it is possible to easily transport the liver 9 while suppressing the application of pressure to the films. The inside of the outer casing 3 may be filled with a preservation solution, together with the organ container 1. The outer casing 3 may also have a warm retaining function and a thermal insulating function in order to maintain the internal temperature constant.

In the example in FIG. 6, the outer casing 3 is fixed to a pair of relay tubes 61 and 62. One ends of the relay tubes 61 and 62 are located outside the outer casing 3. The one ends of the relay tubes 61 and 62 are provided respectively with connectors 611 and 621, each having a push button for release. This structure enables the user to disconnect and connect the connectors 611 and 621 of the relay tubes 61 and 62 by one touch respectively from and to external tubes 71 and 72 that respectively have corresponding connectors 711 and 712.

The other ends of the relay tubes 61 and 62 are located inside the outer casing 3. The other ends of the relay tubes 61 and 62 are provided respectively with connectors 612 and 622, each having a push button for release. Moreover, the external ends of the supplying tube 91 and the drain tube 92 are provided respectively with connectors 911 and 921 that correspond respectively to the connectors 612 and 622. This enables the user to disconnect and connect the connector 612 of the relay tube 61 by one touch from and to the connector 911 of the supplying tube 91. The user is also able to disconnect and connect the connector 622 of the other relay tube 62 by one touch from and to the connector 921 of the drain tube 92.

By employing the above-described connector structure, it is possible to connect and disconnect the tubes while maintaining the insides of the tubes clean. In organ transplantation operations, quick treatment is extremely important. Combined use of the above-described connector structure and the organ container 1 enables more reliably and more quickly advancing organ transplantation operations. Note that the above-described connector structure may be provided only either outside or inside the outer casing 3.

Similarly, the organ container 2 of the second embodiment may also be accommodated in the outer casing 3.

The above first and second embodiments describe the organ containers that accommodate the liver 9. However, these organ containers may be configured to accommodate organs other than the liver 9, such as a heart, a pancreas, or a kidney. In the above-described first and second embodiments, the liver 9 is connected to the two tubes 91 and 92. However, the number of tubes connected to an organ may be one, or may be three or more.

Components described in the above embodiments and variations may be appropriately combined appropriately within a range that causes no contradictions.

REFERENCE SIGNS LIST 1, 2 Organ container
3 Outer casing
9 Liver
11 First film
12 Second film
21 Lower frame
22 Upper frame
23 Locking part
24 Groove
30 Film bag
31 Opening
40 Chuck
41 Chuck member
42 Projection and depression
43 Groove 50 Drawstring
61, 62 Relay tube
91 Supplying tube
92 Drain tube

The invention claimed is:

1. An organ container that accommodates an organ, comprising: a flexible film that holds said organ; an opening and closing part that opens and closes an edge of said film; and a tube holder that holds a tube extending between said organ in said film and an outside of said film;
  - wherein said film incudes: a sheet-like first film that covers a lower part of said organ; and a sheet-like second film that covers an upper part of said organ, and said organ is sandwiched and held between said first film and said second film; and
  - wherein said opening and closing part includes: a ring-shaped lower frame that supports peripheral portions of said first film and said second film from an underside, the peripheral portions overlapping each other; and a ring-shaped upper frame that sandwiches said peripheral portions of said first film and said second film with said lower frame.

2. The organ container according to claim 1, further comprising: a locking part that locks and fixes said lower frame and said upper frame to each other by bringing said lower frame and said upper frame close to each other.

3. The organ container according to claim 1, wherein said tube holder has a groove provided in at least one of an upper face of said lower frame and a lower face of said upper frame, and said tube is fitted in said groove.

4. The organ container according to claim 3, wherein
  said tube holder has a plurality of grooves, each of which is said groove, and
  said plurality of grooves are provided at intervals in a circumferential direction.

5. The organ container according to claim 1, wherein said film is made of a resin.

* * * * *